United States Patent [19]

Cucinella et al.

[11] 4,278,611

[45] Jul. 14, 1981

[54] PROCESS FOR SYNTHESIZING ALKOXYALANATES OF ALKALINE EARTH METALS

[75] Inventors: Salvatore Cucinella, San Donato Milanese; Giovanni Dozzi, Milan, both of Italy

[73] Assignee: Anic S.p.A., Palermo, Italy

[21] Appl. No.: 108,225

[22] Filed: Dec. 28, 1979

[30] Foreign Application Priority Data

Jan. 8, 1979 [IT] Italy ................................ 19125 A/79

[51] Int. Cl.$^3$ ............................................... C07F 5/06
[52] U.S. Cl. .............................................. 260/448 AD
[58] Field of Search ................................. 260/448 AD

[56] References Cited

U.S. PATENT DOCUMENTS

| | | | |
|---|---|---|---|
| 1,689,356 | 10/1928 | Meerwein | 260/448 AD |
| 3,060,216 | 10/1962 | Hamprecht et al. | 260/448 AD |
| 3,147,272 | 9/1964 | Brown et al. | 260/448 AD X |
| 3,281,443 | 10/1966 | Hunt | 260/448 AD |
| 3,394,158 | 7/1968 | Chini et al. | 260/448 AD |
| 3,631,083 | 12/1971 | Hartmann | 260/448 AD |
| 3,761,500 | 9/1973 | Thomas | 260/448 AD |
| 3,903,122 | 9/1975 | Thomas | 260/448 AD |
| 4,120,883 | 10/1978 | Sakurai et al. | 260/448 AD X |
| 4,146,549 | 3/1979 | Aishima et al. | 260/448 AD X |

*Primary Examiner*—Helen M. S. Sneed
*Attorney, Agent, or Firm*—Morgan, Finnegan, Pine, Foley & Lee

[57] ABSTRACT

A method for the preparation of alkoxyalanates of alkaline earth metals is disclosed, which comprises the step of reacting an alcoholate of an alkaline earth metal and an alkaline earth metal alanate and an aluminum alcoholate, the reaction being of the additive type.

The products thus obtained are effective catalysts for reactions of reduction, more particularly of hydrogenation of a number of organic compounds.

8 Claims, No Drawings

PROCESS FOR SYNTHESIZING ALKOXYALANATES OF ALKALINE EARTH METALS

This invention relates to a process for synthesizing alanates of alkaline earth metals of general formula:

$$M[AlH_{4+n}(OR)_n]_2$$

starting from the alanate of an alkaline earth metal, an alcoholate of the alkaline earth metal and an aluminium alcoholate, in accordance with the following general reaction (1):

$$xM(AlH_4)_2 + yM(OR)_2 + 2yAl(OR)_3 \rightarrow zM[AlH_{4-n}(OR)_n-2] \quad (1)$$

in which
 (a) $z = x+y$; $n = (4 \cdot y)/z$;
 (b) M = alkaline earth metal
 (c) OR is an alkoxy group of a primary, secondary or tertiary aliphatic, cycloaliphatic or aromatic alcohol, possibly amino or alkoxy-substituted.

The stability and solubility of the products obtained are favoured by:
 (1) the use of a branch chain aliphatic or cycloaliphatic alcohol, or of amino or alkoxy-substituted alcohols;
 (2) values of $n \geq 1.5$. The maximum value of n is 3.5 in order to obtain molecularly defined compounds containing hydride hydrogens.

Complexes of the alanate of the alkaline earth metal with tetrahydrofuran are generally used as the starting substance, and the corresponding alkoxy alanate can retain complexed tetrahydrofuran molecules.

The reaction proceeds in solvents which are inert to hydride hydrogen. Ether, aromatic and aliphatic hydrocarbon solvents can be used for this purpose.

The reaction temperature can be between $-40°$ C. and the product decomposition temperature, which is generally close to or exceeding 150° C.

It is preferable to operate at a temperature between 15° C. and the boiling point of the reaction solvent at atmospheric pressure.

According to the present invention, it is also possible to replace the alkaline earth metal alcoholate used as the starting substance in reaction 1 by its potential precursors, such as a mixture of a halide of the alkaline earth metal and an alkali metal alcoholate (reaction 2), without this altering the nature of the final alkoxyalanate of the alkaline earth metal.

$$xM(AlH_4)_2 + yMX_2 + 2yM'OR + 2yAl(OR)_3 \rightarrow zM[AlH_{4-n}(OR)_n]_2 + 2yM'X \quad (2)$$

in which X = halogen; M' = alkaline metal, and the other symbols or subscripts have the same meaning as for reaction 1. Instead of aluminium alcoholates, it is also possible to use a mixture of two potential precursors such as an aluminium halide and an alkali metal alcoholate.

Whatever the chosen type of reagent, it is important to emphasize that the operational conditions do not change substantially from those of reaction 1.

Thus, it is still possible to proceed in solvents which are inert to hydride hydrogen. Ether, aromatic and aliphatic hydrocarbon solvents can be used for this purpose. The reaction temperature can be between $-40°$ C. and the product decomposition temperature. However, in order to accelerate the reaction it is preferable to operate at the solvent boiling point at atmospheric pressure, possibly using an excess of the alkaline earth metal halide.

EXAMPLE 1

Operating in a nitrogen atmosphere, tetrahydrofuran (80 ml) and Mg(AlH$_4$)$_2$.4THF (20.2 moles) are placed in that order in a 500 ml flask fitted with a mechanical stirrer, condenser and dropping funnel. A mixture of Mg(O.i.C$_3$H$_7$)$_2$ (12.15 mmoles) and Al(O.i-C$_3$H$_7$)$_2$ (24.3 mmoles) in tetrahydrofuran (70 ml) is then added slowly (over 0.5 hours) to the stirred suspension. It is kept stirring at boiling point for 5 hours, to give a practically clear solution in which Al, Mg and active H are analysed. The following molar ratios are found:

$$Mg/Al = 0.55; \ H \ act./Al = 2.46$$

which are in accordance with the formation of $$Mg[AlH_{2.5}(O.i.C_3H_7)_{1.5}]_2.$$

EXAMPLE 2

Operating in a nitrogen atmosphere, methyl tert.butyl ether (60 ml), Mg(AlH$_4$)$_2$.4THF (16.5 mmoles) and Mg(O.t.C$_4$H$_9$)$_2$ (16.5 mmoles) are placed in that order into a 500 ml flask fitted with a magnetic stirrer, condenser and dropping funnel.

The stirred mixture is raised to boiling point, and a solution of Al(O.t.C$_4$H$_9$)$_3$ (33.1 mmoles) in methyl tert.butyl ether is then added slowly (over 0.5 hours).

It is allowed to boil for three hours, and the atomic Mg/Al ratio in the solution is checked, and found to be close to 0.5.

The solution is filtered to remove turbidity, and evaporated under reduced pressure. The solid white residue is dried (10 hours; $1.10^{-3}$ mm Hg; ambient temperature) and analysed.

Found: Al = 12.4%; Mg = 5.7%; H act. = 9.6 meq/g. Calculated for Mg[AlH$_2$(O.C$_4$H$_9$)$_2$]$_2$.THF: Al = 12.1%; Mg = 5.4%; H act. = 9.0 meq/g.

The yield is 98%.

EXAMPLE 3

Operating in a nitrogen atmosphere, toluene (100 ml), Mg(AlH$_4$)$_2$. 4THF (16.55 mmoles) and Mg(O.t.C$_4$H$_9$)$_2$ (16.55 mmoles) are placed in that order in a 500 ml flask fitted with a magnetic stirrer, condenser and dropping funnel.

The mixture is heated to 80° C. while stirring, and a solution of Al(O.t.C$_4$H$_9$)$_3$ (33.1 mmoles) in toluene (50 ml) is then added slowly (over 0.5 hours). It is kept at 80° C. for three hours under stirring, and the atomic Mg/Al ratio in the solution is then checked, and found to be 0.52.

The resultant solution is filtered to remove turbidity, and then evaporated under reduced pressure. The white solid residue is dried (20 hours; $1.10^{-3}$ mmHg; ambient temperature) and analysed.

Found: Al = 12.4%; Mg = 5.6%; H act. = 9.5% meq/g. Calculated for Mg[AlH$_2$(O.C$_4$H$_9$)$_2$]$_2$.THF: Al = 12.1%; Mg = 5.4%; H act. = 9.0 meq/g.

The yield is quantitative.

EXAMPLE 4

Operating in a nitrogen atmosphere, toluene (80 ml), Mg(AlH$_4$)$_2$.4THF (5 mmoles) and Mg(O.i.C$_3$H$_7$)$_2$ (15 mmoles) are placed in that order in a 500 ml flask fitted with a magnetic stirrer, condenser and dropping funnel.

A solution of Al(O.i.C$_3$H$_7$)$_3$ (30 mmoles) in toluene (80 ml) is added slowly (over 0.5 hours) to the stirred mixture at ambient temperature. 1.5 hours after finishing adding the solution, the molar Mg/Al ratio in the solution is determined and is found to be 0.38; after three hours it is found to be 0.40; after eight hours 0.43; and after fourteen hours 0.49. It is filtered to remove turbidity, the clear solution is evaporated and the residue is dried (ten hours; 1.10$^{-4}$ mmHg; ambient temperature) to give a waxy product which was analysed.

Found: Al=12.2% Mg=5.7%; H act.=3.8 meq/g
Calculated for Mg[AlH(OC$_3$H$_7$)$_3$]$_2$. THF: Al=11.8% Mg=5.3%; H act.=4.3 meq/g.

The yield is practically quantitative.

EXAMPLE 5

Operating in a nitrogen atmosphere, tetrahydrofuran (150 ml), Ca(AlH$_4$)$_2$.4THF (36.3 mmoles), CaCl$_2$ (36.3 mmoles) and NaO.i.C$_3$H$_7$ (72.6 mmoles) are placed in that order in a 500 ml flask fitted with a magnetic stirrer, condenser and dropping funnel. The mixture is raised to boiling point, and a solution (100 ml) of Al(O.i.C$_3$H$_7$)$_3$ (72.6 mmoles) is then added slowly (over one hour). It is kept boiling for eight hours, and the atomic Ca/Al ratio in the solution is then checked and found to be 0.41.

An excess of CaCl$_2$ (11.4 mmoles) is added, and boiling continued for a further five hours. The Ca/Al ratio in the solution is then 0.47.

It is filtered, and the solution together with the wash solvent is evaporated and the solid product dried (ten hours; 1.10$^{-3}$ mmHg; ambient temperature) and analysed.

Found: Al=11.5%; Ca=8.1%; H act.=8.1 meq/g
Calculated for Ca[AlH$_2$(OC$_3$H$_7$)$_2$]$_2$.2THF: Al=11.3%; Ca=8.4%; H act=8.4 meq/g The yield is 95%.

EXAMPLE 6

Operating in a nitrogen atmosphere, tetrahydrofuran (45 ml), Ca(AlH$_4$)$_2$.4THF (10 mmoles), CaCl$_2$ (11 mmoles) and NaO.t.C$_4$H$_9$ (20 mmoles) are placed in that order into a 500 ml flask fitted with a magnetic stirrer, condenser and dropping funnel. The stirred mixture is raised to boiling point and a solution (45 ml) of Al(O.t.C$_4$H$_9$)$_3$ (20 mmoles) in tetrahydrofuran is then added slowly (over one hour). Boiling is maintained, and the atomic Ca/Al ratio in the solution is checked, and found to be 0.37 (after 0.5 hours), 0.4 (1.5 hours), 0.46 (4.5 hours), and 0.48 (six hours).

It is finally filtered, and the solution together with the wash solvent is evaporated and the white solid residue dried (ten hours; 1.10$^{-4}$ mmHg; ambient temperature) and analysed.

Found: Al=1.50%; Ca=7.5%; H act.=7.5 meq/g.
Calculated for Ca[AlH$_2$(O.C$_4$H$_9$)$_2$]$_2$.2THF: Al=10.5%; Ca=7.5%; H act.=7.5 meq/g The yield is 90%.

EXAMPLE 7

Operating in a nitrogen atmosphere, tetrahydrofuran (100 ml), Ca(AlH$_4$)$_2$.4THF (20.8 mmoles), CaCl$_2$ (23 mmoles) and NaOC$_6$H$_{11}$ (41.6 mmoles) are placed in that order in a 500 ml flask fitted with a magnetic stirrer, condenser and dropping funnel. The mixture is raised to boiling point and a solution of Al(OC$_6$H$_{11}$)$_3$ (41.6 mmoles) in THF (65 ml) is then slowly added (over 0.5 hours). Boiling is maintained, and the atomic Ca/Al ratio in the solution is checked.

After 4.5 hours, the Ca/Al=0.43. An excess of CaCl$_2$ (6.6 mmoles) is added. After a further 5.5 hours at boiling point, the Ca/Al in the solution=0.46. It is filtered, and the solution including the wash solvent is evaporated and the white solid residue dried (ten hours; 1.10$^{-4}$ mmHg; ambient temperature) and analysed.

Found: Al=8.6%; Ca=5.9%; H act.=6.1 meq/g
Calculated for Ca[AlH$_2$(O.C$_6$H$_{11}$)$_2$]$_2$.2THF: Al=8.4%; Ca=6.3%; H act.=6.3 meq/g.

The yield is 98%.

EXAMPLE 8

Operating in a nitrogen atmosphere, tetrahydrofuran (150 ml), Ca(AlH$_4$)$_2$.4THF (35.9 mmoles), CaCl$_2$ (35.9 mmoles) and NaOCH$_2$CH$_2$OCH$_3$ (71.8 mmoles) are placed in that order in a 500 ml flask fitted with a mechanical stirrer, condenser and dropping funnel. The mixture is raised to boiling point, and a solution (80 ml) of Al(OCH$_2$CH$_2$OCH$_3$)$_3$ (71.8 mmoles) in tetrahydrofuran is then slowly added (over 0.5 hours). Boiling is maintained, and the atomic Ca/Al ratio in the solution is checked and is found to be 0.37 after ten hours. An excess of CaCl$_2$ (13.8 mmoles) is added, and boiling is maintained for a further six hours. The atomic Ca/Al ratio in the solution is then 0.51. It is filtered, the solution together with the wash solvent is evaporated and the white solid residue is dried and analysed.

Found: Al=12.4%; Ca=9.0%; H act.=8.9 meq/g.
Calculated for Ca[AlH$_2$(OCH$_2$CH$_2$OCH$_3$)$_2$]$_2$.0.5THF: Al=12.4%; Ca=9.2%; H act.=9.2 meq/g.

The yield is 90%.

EXAMPLE 9

Operating in a nitrogen atmosphere, ethyl ether (80 ml), NaOCH$_2$CH$_2$OCH$_3$ (26.5 mmoles), Ca(AlH$_4$)$_2$.4THF (13.25 mmoles) and CaCl$_2$ (26.5 mmoles) are placed in that order in a 500 ml flask fitted with a magnetic stirrer, condenser and dropping funnel. The stirred mixture is raised to boiling point and a solution of Al(OCH$_2$CH$_2$OCH$_3$)$_3$ (26.5 mmoles) in ethyl ether (80 ml) is then slowly added (over 30 minutes). Boiling is maintained under stirring for one hour, and the atomic Ca/Al ratio in the solution is checked and is found to be 0.3. After a further four hours, the Ca/Al ratio is 0.39. An excess of CaCl$_2$ (7 mmoles) is then added, and the mixture is refluxed for two hours, with the result that the Ca/Al rises to 0.42. After adding a further excess of CaCl$_2$ (16 mmoles) and after a further five hours of reflux, the Ca/Al ratio is 0.45. It is filtered, the clear solution including the wash solvent is evaporated under reduced pressure, and the white solid residue is dried (one hour; 1.10$^{-3}$ mmHg; ambient temperature) and analysed.

Found: Al=13.0%; Ca=8.5%; H act.=9.5 meq/g.
Calculated for Ca[AlH$_2$(OCH$_2$CH$_2$OCH$_3$)$_2$]$_2$: Al=13.4%; Ca=9.5%; H act.=9.8 meq/g.

The yield is 70%.

EXAMPLE 10

Operating in a nitrogen atmosphere, tetrahydrofuran (100 ml), CaCl$_2$ (25 mmoles), NaOC$_6$H$_{11}$ (33.3 mmoles), and Al(OC$_6$H$_{11}$)$_3$ (33.3 mmoles) are placed in that order in a 500 ml flask fitted with a magnetic stirrer, condenser and dropping funnel. The stirred mixture is raised to boiling point, and a solution of Ca(AlH$_4$)$_2$ (10 mmoles) in tetrahydrofuran (70 ml) is then slowly added (over 30 minutes). Boiling is maintained under stirring for about 1.5 hours, and the molar Ca/Al ratio in the solution is checked and found to be 0.49. The suspension is filtered, and the clear solution including the wash solvent is evaporated under reduced pressure to give a product in the form of a white solid residue which is dried (ten hours; $1.10^{-4}$ mmHg; ambient temperature) and analysed.

Found: Al=6.7%; Ca=5.0%; H act.=3.7 meq/g. Calculated for Ca[AlH$_{1.5}$(OC$_6$H$_{11}$)$_{2.5}$]$_2$.3THF: Al=6.7%; Ca=4.9%; H act.=3.7 meq/g.

The yield is 93%.

We claim:

1. A process for synthesizing alkoxyalanates of alkaline earth metals of the formula:

$$M[AlH_{4-n}(OR)_n]_2$$

in which M represents an alkaline earth metal, OR represents an alkoxy group of a primary, secondary or tertiary aliphatic, cycloaliphatic or aromatic alcohol, the radical R being simple or amino or alkoxy-substituted, and n is a number between 1.5 and 3.5, the process consisting of reacting an alanate of the alkaline earth metal with an alcoholate of the alkaline earth metal and an aluminum alcoholate in an inert solvent at a temperature between −40° C. and the product decomposition temperature.

2. A process as claimed in claim 1, wherein said inert solvent is chosen from ethers or aliphatic or aromatic hydrocarbons.

3. A process as claimed in claim 1, wherein said temperature is from the range of 15° C. to the solvent boiling point.

4. The process of claim 1 wherein said alkaline earth metal alanate is complexed with tetrahydrofuran.

5. The process of claim 1 wherein in place of said alkaline earth metal alcoholate, a precursor thereof is added.

6. The process of claim 5 wherein said alkaline earth metal alcoholate precursor comprises a mixture of an alkaline earth metal halide and an alkali metal alcoholate.

7. The process of claim 1 wherein in place of said aluminium alcoholate, a precursor thereof is added.

8. The process of claim 7 wherein said aluminium alcoholate precursor comprises a mixture of an aluminium halide and an alkali metal alcoholate.

* * * * *